(12) United States Patent
Goldstein et al.

(10) Patent No.: US 6,455,306 B1
(45) Date of Patent: Sep. 24, 2002

(54) TRANSFUSABLE OXYGENATING COMPOSITION

(75) Inventors: Walter Elliott Goldstein, Foster City, CA (US); Warren Keene Miller, Lincoln University, PA (US)

(73) Assignee: Transcyte, Inc., Farmville, VA (US)

( * ) Notice: Subject to any disclaimer, the term of this patent is extended or adjusted under 35 U.S.C. 154(b) by 14 days.

(21) Appl. No.: 09/590,376

(22) Filed: Jun. 9, 2000

(51) Int. Cl.[7] .................................................. C12N 5/00
(52) U.S. Cl. ........................... 435/372; 435/2; 435/325; 424/93.73
(58) Field of Search ................................. 435/372, 325, 435/2; 424/93.73

(56) References Cited

U.S. PATENT DOCUMENTS

| | | |
|---|---|---|
| 3,942,527 A | 3/1976 | Li |
| 4,919,895 A | 4/1990 | Heldebrant et al. |
| 5,510,262 A | 4/1996 | Stephanopoulos et al. |
| 5,599,705 A * | 2/1997 | Cameron |
| 5,811,301 A * | 9/1998 | Cameron |

* cited by examiner

*Primary Examiner*—Leon B. Lankford, Jr.
(74) *Attorney, Agent, or Firm*—Rothwell, Figg, Ernst & Manbeck (57) ABSTRACT

The present invention relates to a process for producing a transfusable, oxygenating composition of human red blood cells by the ex vivo culturing, expansion and differentiation of human primitive hematopoietic cells. The process involves expansion of primitive hematopoietic cells in a first bioreactor containing one or more growth factors, differentiating the cells into erythroid progenitor cells in a second bioreactor containing one or more differentiation factors and effecting maturation of the erythroid progenitor cells into mature erythrocytes in a third bioreactor containing one or more maturation factors. The invention also provides a process for producing a transfusable, oxygenating composition of red blood cells by expansion and differentiation of primitive hematopoietic cells in a bioreactor containing a nutrient medium which includes perfluorocarbons which improve the exchange of oxygen and carbon dioxide between the cells and the nutrient media.

22 Claims, 4 Drawing Sheets

TRANSFUSABLE OXYGENATING COMPOSITION

BACKGROUND OF THE INVENTION

A. Technical Field

This invention relates to a transfusable composition of cells produced by ex vivo growth processes. More particularly, it relates to transfusable compositions that are universally compatible, perform the same physiologic function as red blood cells ("rbcs" or "erythrocytes") from human donors, and supplement or replace the current practice of transfusing red blood cells from human donors.

B. Background Art

1. Current Blood-Banking Practice

Blood transfusion is a critical component of current medical practice. Each year there are about 12 million donation units transfused in the United States. Of these, 3.2 million units are used to treat chronic anemia, 8 million units are used to treat surgical blood loss and about 750,000 units are used to treat traumatic blood loss. As practiced currently, blood transfusion involves drawing blood from a presumed healthy donor, mixing it with an anticoagulant/preservative, testing it for immunologic reactivity (typing), testing it for known infectious agents (currently eight) and storing it for administration to suitable recipient/patient. Prior to administration to the recipient, a sample of the donor blood is tested in combination with a sample of the recipient's blood to determine immunologic compatibility (cross-matching). After establishing compatibility, the donated blood is intravenously infused into the recipient. Despite the testing precautions, blood transfusions pose life-threatening risks to the recipient. Epstein, *Increasing Safety of Blood Transfusions,* Amer. Red Cross (1992).

Although there are recognized therapeutic applications for white blood cells, platelets and other components of blood, e.g. coagulation factors, plasma proteins. etc., the predominate use for blood transfusions is based on the oxygen-carrying ability of the red blood cells. A unit of whole blood is 500 milliliters or approximately one pint. Adults have from about 9 to about 12 pints of blood in their bodies. Blood donated for transfusion is typically composed of 40–50% (by volume) red blood cells and 50–60% plasma (liquid component). One milliliter of blood typically contains 4 to 5 billion rbcs, which is equivalent to 2.0 to 2.5 trillion rbcs per donation unit.

Blood typing is the process by which red blood cells are tested to determine which cell surface antigens are present and absent. It is standard blood-banking practice to test routinely for the A, B, and D (Rh) antigens and to test for other antigens only in selected cases. When a person lacks a particular red blood cell antigen, his or her plasma may contain an antibody to that antigen. Some antibodies (e.g. anti-A and anti-B) are naturally occurring and are expected to be present. Other antibodies are unexpected. They usually result from a challenge to the immune system by exposure to foreign blood cells, such as through transfusion or pregnancy. A small percentage of persons carry antibodies to certain blood cell antigens without prior exposure.

Antibody reactions with antigens present on infused red cells often result in a serious adverse clinical event known as a "transfusion reaction." With the exception of the ABO blood group system, the kinds of antibodies that cause transfusion reactions are found almost exclusively in persons who have had prior transfusions or pregnancies. Antibodies in the patient's plasma are detected in screening studies using panels of red cells containing known antigens. Blood group antigens are glycoprotein or glycolipid structures on the surface of the red cell membrane and can be removed or modified in potency by using various enzymes, e.g. glycosidases, proteases, etc. Red cell antigens vary in their immunogenicity and prevalence.

In routine blood-banking practice, only ABO typing and Rh grouping are performed. A crossmatch procedure is performed as a final check for compatibility.

Crossmatching is performed by mixing the donor's cells with the recipient's serum, with and without enhancing agents, and observing for agglutination (clumping) or lysis (destruction) of the red cells. Either of these events signals that a problem antibody to an antigen on the donor's cells is present in the recipient's plasma and signals the likelihood of a transfusion reaction.

The frequency and identity of problem antibodies/blood types have been established (in order of decreasing frequency):

1. Anti-D (with or without anti-C or anti-E);
2. Anti-$Le^a$ and anti-$Le^b$ (alone or together);
3. Anti-K;
4. Anti-E anti-$P_1$;
5. Anti-c, Anti-cE, Anti-$Fy^a$, Anti-M;
6. Anti-$jK^a$, Anti-S;
7. Anti-Ce, anti-E;
8. Anti-$jK^b$, anti-N, Anti-s. anti-$Fy^b$.

Because of a variable and uncertain supply (often critical shortages), the potential for transmitting blood-borne disease, and the risk of immunologic incompatibilities and transfusion reactions, there is a recognized and substantial need to supplement or replace the current practice of transfusing blood from human donors.

2. Ex Vivo Cell Culture

Mature blood cells result from the growth and differentiation of hematopoietic cells. Hematopoietic cells are generated from pluripotent stem cells, which can both self-renew and give rise to hematopoietic progenitor cells. Hematopoietic progenitor cells include lymphoid, mixed-lineage colony-forming units (CFU-Mix), granulocyte/macrophage colony-forming units (CFU-GM), erythrocyte burst-forming units (BFU-E), and megakaryocyte burst-forming units (BFU-meg). These progenitors, in turn, give rise to mature blood cells. (Koller et al., *Biotechnol. Bioeng.* 42: 477 (1993).

Primitive hematopoietic cells reside in the bone arrow of normal adults, where they mature into functional blood cells and are released into the peripheral circulation. The bone marrow is a complex environment consisting of stem, progenitor and mature hematopoietic cells, along with accessory cells and molecules (in extracellular matrix) which are necessary to maintain the process of hematopoiesis. Accessory cells and the extracellular matrix mediate the differentiation and proliferation of hematopoietic cells by producing growth factors and by direct cell contact. Bone marrow, thus, is a natural source of hematopoietic cells at various stages of differentiation, as well as a source of accessory cells. Immature hematopoietic cells can also be harvested from peripheral blood, with or without stimulation by growth factors, using leukopharesis. This process separates the nucleated cells of interest from red blood cells and plasma. Another source of immature hematopoietic cells is umbilical cord blood. Bone marrow has been the traditional source of hematopoietic cells for transplantation therapies, although peripheral blood progenitor cell transplants have also proven useful. Demuynck, et al., *Ann. Hematol.* 71: 29 (1995).

Cancer chemotherapy often results in severe damage to hematopoietic progenitor cells. As a result, the patient is susceptible to infection and bleeding. A therapy for this damage involves transplantation of bone marrow or hematopoietic cells. The loss of hematopoietic activity, due to damage by chemotherapy, can be offset by infusing hematopoietic cells into the patient after chemotherapy. Thus, there has been much interest and in harvesting and expanding hematopoietic progenitor cells in ex-vivo cell cultures.

Ex vivo expansion of hematopoietic progenitor cells can decrease the amount of the initial harvest necessary for successful engraftment and, most importantly, can improve the transplant outcome by allowing more cells to be transplanted. Such expansion supplements transplants with mature progenitors and speeds the recovery of mature white cells and platelets, which in turn fight infection and control bleeding, respectively. In addition, ex vivo expansion also allows the use of a single hematopoietic cell harvest for repeated transplants over an extended period of time. Collins. et al., *Curr. Opin. in Biotechnol.*, 7: 223 (1996).

Ex vivo expansion of hematopoietic cells includes the following prerequisites: First, cells positive for the CD34 antigen are extracted because these cells are presumed to represent the most primitive hematopoietic cells. Second, the extract is further purified for $CD34^+$ cells having other antigens associated with the desired progeny. Third, selected cells are added to growth media, with or without exogenous growth factors and with or without serum. Fourth, the cell/growth medium is incubated in a bioreactor to control the environment for expansion and/or the differentiation of primitive or mature hematopoietic cells. Finally, the expanded and differentiated cells are harvested and purified.

While all of these prerequisites are routinely practiced for providing hematopoietic cells for bone marrow transplantation, a transfusable composition of oxygenating cells produced by the ex vivo culture of hematopoietic cells is still not available. In fact, the current state of the art of hematopoietic cell culture is directed away from erythropoiesis (production of red blood cells) in favor of producing infection-fighting white blood cells (leukopoiesis) and platelets to control bleeding.

3. Bioreactors

Bioreactors are systems that provide an environment for the growth, expansion and differentiation of cells in culture. Bioreactor systems have been described as static, perfusion, and stirred suspension systems. Static culture systems, such as culture well plates and flasks are the most popular means for expanding hematopoietic cells. Koller, et al., *Biotechnol. Bioeng.*, 50: 505 (1996). However, these systems present significant difficulties in controlling nutrient concentrations and waste product concentrations and cannot support high cell densities. Although exchanging as much as 50% of the medium has been effective in increasing total cell production, exchange of all the medium does not increase culture performance, presumably due to the removal of coincidental growth factors or the disruption of cell-to-cell interactions.

Perfusion systems have been developed to exchange the culture medium continuously without mechanically damaging cells or reducing the concentration of critical factors. Sandstrom, et al., *Biotechnol. Bioeng.*, 50: 493 (1996). Such perfusion systems have shown greater cell expansion than static systems and have successfully expanded human bone marrow progenitor cells, CFU-GM and BFU-E. Cameron, R. B., U.S. Pat. Nos. 5,599,705 and 5,811,301, describes in vitro production of what are said to be transfusable differentiated, universally compatible human blood cells by expansion of pluripotent hematopoietic stem cells in perfusion type bioreactors, such as those having ceramic matrix cores, hollow capillary fibers or protein-coated microspheres.

Stirred vessels have been suggested as the system of choice for many mammalian cell culture applications, because they offer advantages in sampling, data collection and control of medium conditions. Zandstra, et al., *Biotechnology*, 12:909 (1994). Nevertheless, the adaptation of these stirred systems to hematopoietic cell cultures has proven to be a challenge, because of the uncertain effect of stirring on the disruption of cell-to-cell associations common to these types of cultures.

4. Perfluorocarbons

Because cell cultures involve living processes, respiration at the cellular level must be supported. Respiration for mammalian cells involves the exchange of essentially two gases, oxygen and carbon dioxide. Depending on the specific configuration of the bioreactor, gas transport to each cell growing in the bioreactor, can be impeded by the cell growth density (cell accumulation) and the oxygen-carrying capacity and distribution of the medium. Koller, et al., *Biotechnol. Bioeng.*, 42:477 (1993). Perfluorocarbons ("PFCs"), particularly perfluorodecalin and perfluorooctane, have been demonstrated to carry as much as four times the amount of oxygen as water. Also, their oxygen transport capacity is directly proportional to their concentration and $pO_2$. Riess, I. G., *Vox Sang.*, 61:225 (1991).

Because PFCs dissolve gases, such as oxygen and carbon dioxide, to a greater extent than aqueous culture media, they aid in transfer of oxygen to and removal of carbon dioxide from cells. They also are very compatible with mammalian cells. These features obviate the need to provide excessive gas to the medium for oxygenation of cells and waste gas removal. The use of PFCs as a means optimally to regulate oxygenation or regulate mixing kinetics in bioreactors have not been utilized for production of transfusable differentiated blood cells obtained by in vitro.

PFCs are typically introduced into aqueous media as emulsions. Not only do the emulsions serve to transport dissolved gases, they can also increase the viscosity of the media, thereby presenting an alternative method to control the rheology or mixing kinetics of the cell culture. For optimal control, the viscosity should be high enough to form a protective shield against shear impulses, but not so high as to impose a detrimental barrier to mass transfer for supply of nutrients or removal of waste products. Because ex vivo erythropoiesis occurs in different phases of development, each requiring unique growth factors, gas mixtures, and degrees of perfusion, no single bioreactor design has been shown to support the entire process from expansion of the primitive hematopoietic cell through expansion and differentiation of erythroid (referring to red blood cells) progenitors to the maturation of mature transfusable erythrocytes.

SUMMARY OF THE INVENTION

In accordance with this invention, a process for producing a transfusable, oxygenating composition of red blood cells comprises:

(a) expanding a culture of purified primitive hematopoietic cells in a first bioreactor in the presence of growth factors and under conditions that promote self renewal of such cells to increase their numbers without substantial differentiation into committed progenitor cells, thereby producing an expanded culture of purified primitive hematopoietic cells;

(b) effecting differentiation of the primitive hematopoietic cells by culturing said expanded culture of purified primitive hematopoietic cells in a second bioreactor in the presence of differentiation factors and under conditions that promote the differentiation of the primitive hematopoietic cells into erythroid progenitor cells;

(c) producing mature erythrocytes by culturing said erythroid progenitor cells in a third bioreactor in the presence of maturation factors and under conditions that promote the maturation of progenitor erythroid cells into mature erythrocytes; and (d) harvesting said mature erythrocytes and formulating them into transfusable oxygenating composition.

In a preferred embodiment, perfluorocarbons are employed in the culture media used in one or more of the bioreactors. The perfluorocarbons promote transfer of respiratory gases to and from the cells in such culture media.

As discussed below, the various bioreactors may be different vessels arranged in tandem or may be the same vessel with changes in media, added factors and/or conditions. Further, additional bioreactors may be employed in the process, for example, for maintenance and/or storage of cell cultures.

The process of this invention provides a source of transfusable red blood cells that may be universally compatible and free of the risk of contamination with is infectious agents. Because the process is based on in vitro expansion of primitive hematopoietic stem cells obtained, for example, from bone marrow explants, the need for reliance on blood donations is diminished.

DETAILED DESCRIPTION OF THE PREFERRED EMBODIMENT

The present invention relates to transfusable, oxygenating composition of cells, produced using a novel ex vivo growth process. The composition may be immunologically universal and performs the same physiological functions as erythrocytes obtained from human donors.

Unexpectedly, it has been found that cell cultures that have been studied and developed for the purposes of bone marrow transplants and bone marrow reconstitution following aggressive chemotherapy for cancer can be redirected, optimized and processed to yield a transfusable composition of oxygenating cells. Although numerous methods for expanding primitive hematopoietic cells in in vitro cultures are actively being developed, those methods primarily are directed to expanding primitive cells for bone marrow transplantation or differentiating the culture to produce cells to bolster the immune systems of immunocompromised patients. As a result of conditions that are employed to enhance the differentiation and growth of immune-bolstering cells (granulocytes, monocytes and lymphocytes) of the hematopoietic cell culture, the process of erythropoiesis (red blood cell production) is consequentially suppressed, or at least made suboptimal, and uncharacterized with respect to the suitability of the erythroid lineage for transfusable composition.

Typical protocols employed in the process of this invention are described below. It will be appreciated by those skilled in the art that these protocols are illustrative and may be altered to suit the particular situation. Certain of the steps may be omitted and others may be added.

Selecting a Healthy Human Donor of a Universal Blood Type

As a preferred donor, an individual is identified through the National Marrow Donor Registration Program. This individual, either living or as a cadaveric organ donor, is screened by standard blood-banking procedures for the detection of infectious disease. The donor preferably has been extensively typed for blood cell antigens is preferably negative for A, B and Rh red blood cell antigens, and is preferably also negative for $Le^a$, $Le^b$, K, E, $P_1$, c, cE, $Fy^a$, M, $jK^a$, S, Ce, E, $jK^b$, N, s, $Fy^b$ antigens. Cells obtained from such donors yield a transfusable composition of the greatest universality, particularly suited for donations to previously sensitized patients.

Collecting Bone Marrow, Peripheral Blood

As a preferred method, heparinized bone marrow is obtained from informed and consenting individuals. Bone marrow is usually collected under general or spinal anesthesia, during which the iliac crests are aseptically punctured and aspirated multiple times in order to collect 500 to 1000 ml of fluid containing bone marrow and blood cells (McAdams et al., *Trends in Biotechnol.*, 14:388 (1996). Alternatively, bone marrow from cadaveric organ donors is aspirated from the vertebral bodies.

Where bone marrow aspiration is not suitable, peripheral blood is obtained from informed, consenting donors by a process known as aphereis. Using an instrument such as the Cobe Spectra Processor (Denver, Colo.), peripheral blood is drawn from the donor, mononuclear cells are isolated from the blood, and the remaining blood is returned to the donor in a continuous process. Approximately 12 liters of blood are processed over 7–10 sessions of 3–4 hours each, yielding as much as 300 mL of peripheral hematopoietic cells. (Pelehach, L., *Lab. Med.*, 27:588 (1996).

Processing the Collection

Primitive hematopoietic cells thus collected either from bone marrow or peripheral blood harvests are tested for contamination with bacteria. The harvest is also reduced in volume, for example, by adding a solution of 6% hetastarch in 0.9%, sodium chloride to speed the sedimentation of the cells. Red cells settle to the bottom, then a buffy coat, then plasma on top. As many red cells as possible are drained off and the remainder is centrifuged. The plasma is expressed leaving the buffy coat, which contains the primitive hematopoietic cells. Pelehach, L., *Lab. Med.* , 27:588 (1996).

Low-density cells (<1.077 $gm/cm^3$) are isolated from the harvests using Ficoll-Paque (Pharmacia LKB, Uppsala, Sweden), resuspended in Iscove's medium. Iscove, et al., *Exp. Cell. Res.*, 126:121 (1980) with 50% fetal calf serum (FCS) and kept at 4° C. Alternatively, the samples are frozen in Iscove's medium containing 2.5% human serum albumin (HSA) and 10% dimethylsulfoxide (DMSO). Freezing is accomplished in a controlled-rate freezer, equipped with a computer that allows the cells to freeze while the temperature falls at a rate of 1° C. per minute. After freezing, the cells are stored in the vapor phase of liquid nitrogen (<−120° C.). It is important that the cells are frozen slowly, so that ice crystals do not form inside the cells, causing them to rupture.

Pelehach, L., *Lab. Med.*, 27:588 (1996). Frozen samples are rapidly thawed and slowly diluted with Iscove's medium containing 0.1 mg/mL DNAse (Type 11, D4513, Sigma Chem. Co., St. Louis, Mo.) and 2% fetal calf serum (FCS) (A-1111. HyClone Labs, Logan UT). The samples are washed once and resuspended in Hank's hepes-buffered salt solution containing 2% FCS and 0.1% sodium azide (HM) for subsequent staining.

Selecting Primitive Hematopoietic Cells

Three-color cell fluorescence-activated analysis and sorting, in conjunction with fluorescent-labeled monoclonal antibodies specific for hematopoietic cell surface antigens, may be used to purify the harvested bone marrow or peripheral blood. Highly purified primitive hematopoietic cells that exhibit the phenotype CD34+, CD45R Alo, CD71lo have been associated with long-term erythropoiesis in ex vivo cultures. Landsdorp, P. M., Dragowska W., *J. Exp. Med.*, 175: 1501 (1992). IgG1 monoclonal antibodies (mabs) specific for antigens CD34 (designated 8G12), Lansdorp et al., *J. Exp. Med*, 172: 363 (1990), CD45RA (designated 8d2), Lansdorp et al., *Cytometry*, 12: 723 (1991) and CD71 (designated OKT9) Sutherland et al., *Proc. Natl. Acad. Sci. USA*, 78: 4515 (1981) are purified from hybridoma tissue culture supernatant, using protein A or protein G affinity chromatography. Anti-CD34 are labeled with cyanine-5succinimidylester. Southwick, et al., *Cytometry*, 11: 418 (1990). Anti-CD71 are labeled with FITC (F7250. Sigma Chem. Co., St. Louis, Mo.) at a fluorescein/protein ratio of 5.0. Anti-CD45RA are labeled with RPE by mixing with, respectively, monoclonal IgG1 anti-RPE antibody ID3, and RPE at a molecular ratio of 1:1 (Lansdorp et al., *Cytometry*, 12: 72,n3 (1991). Harvests from bone marrow or peripheral blood containing primitive hematopoietic cells ($10^7$/mL) are incubated simultaneously with 8G12-Cy5, 8d2-RPE complexes, and OKT9-FITC at, respectively, 20, 4 and 1 µg/mL for 30 min at 4° C. Controls consist of single-stained suspensions and three-color staining with anti-TNP-RPE complexes instead of 8d2-RPE complexes. Cells are washed twice in HM and resuspended in HM containing 2 µg/mL propidium iodide (P5264, Sigma Chem. Co., St. Louis, Mo.) before sorting. Throughout the procedure, cells are kept at 4° C. Cells are sorted on a FACStar Plus®, (Becton Dickinson Co.) equipped with a 5-W argon and 30-mW helium neon laser. Specific fluorescence of FITC, RPE, PI and Cy5 excited at 488 nm (0.4 W) and 633 nm (30 mW), as well as forward and orthogonal light scatter signals, are used to establish sort windows. Positively for each probe is defined as fluorescence that exceeds 99% of controls. Cells are collected in serum-deprived medium, described below.

Integrating the Bioreactors and Perfluorocarbons Into the Process

Figure 2:
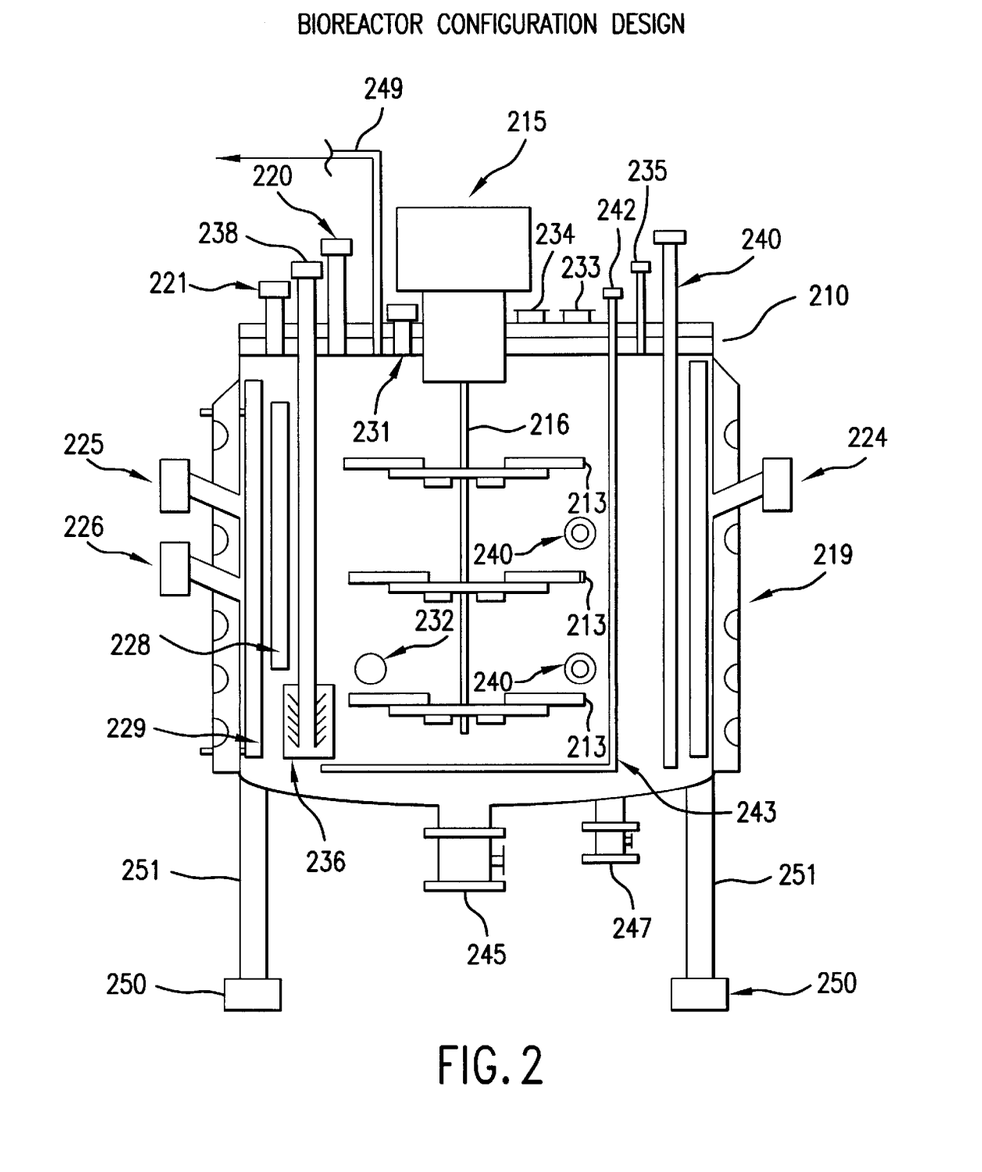
FIG. 2 illustrates the design of a preferred embodiment of bioreactor used in this process.

A bioreactor that may be used in the process of this invention is illustrated in FIG. 2. Bioreactor 210 advantageously includes a cylindrical vessel that is constructed of a corrosion-resistant material, such as 316 stainless steel. The bioreactor may be supported by legs 251 and feet 250, which optionally may include strain gauges (load cells) for measuring the weight of the contents of the bioreactor. It is preferably fitted with a thermally regulated jacket 219 to provide heat transfer for heating or cooling to control temperature. The height-to-diameter ratio of the vessel comprising bioreactor 210 generally ranges from about 3:1 to about 1:1. The vessel is equipped with an agitator, which, as illustrated, typically comprises multiple impellers 213 mounted on a central shaft 216. Shaft 216 may be driven by a magnetic drive 215 which keeps the contents of bioreactor 210 isolated from the drive motor and the exterior of the bioreactor. A magnetic drive, such as that available from Applikon, Inc., 1165 Chess Drive, Suite G, Foster City, Calif. 94404 is preferred. Alternatively, a sterile condensate lubricated mechanical seal, such as that available from the John Crane Co., 6400 West Oakton Street, Morton Grove, Ill. 60053 may be employed to separate the bioreactor interior from the exterior in the region of the drive shaft.

Impellers 213 may have three to four blades each to achieve optimal agitation. For bioreactors having a relatively large height-to diameter ratio, one impeller is preferably used for each section of height which equals the diameter. This design effects uniform mixing throughout the vessel. The impeller is advantageously of the scoping type to effect thorough axial and radial mixing without imposing significant shear forces. The scoping impeller available from ABEC, Allentown, Pennsylvania USA is preferred. The agitators are turned at the minimum speed required to keep the cells suspended without violently mixing them.

Bioreactor 210 also preferably includes baffles 229 to minimize swirling and poor mixing. The baffles preferably have a round or oblong shape to effect minimal shear while enhancing mixing by the. interruption of the flow path of the liquid contents.

Bioreactor 210 is typically equipped with steam-blocked ports 220 and 221 for adding materials and with steam-blocked ports 240 and 247 for sampling. The steam-blocked ports are designed to provided automatic sterilization before and after samples are taken. Ports designed for inoculation are suitably steam-blocked to prevent contamination on transfer of cells. Inoculation ports optionally may be designed for sterile attachment of an inoculation bottle, in which case, the connections between the inoculum bottle and the port are sterilized prior to use.

Bioreactor 210 may also have various means for adding and removing liquid and gaseous materials. For example, port 235 may be used for pressurizing bioreactor 210 with an inert gas to facilitate discharge of materials. The liquid component of the contents of the bioreactor may then be discharged through self-cleaning filter 236 and exit port 238. Non-filtered biomass may be discharged through discharge port 240, located at the top of the vessel. Port 242 may be used for introducing gases or liquids, such as perfluorocarbons (e.g. in the form of perfluorocarbon emulsions), which are distributed in the bioreactor through perforated sparging line 243. Sterilizable valves may be provided at the bottom of bioreactor 210 for harvesting the contents either under gravity flow (valve 245) or by pumping out the contents (valve 247). Valve 247 exists in duplicate in different sizes to accommodate sampling and pumping out contents. Gas exhaust port 249 may be used for venting excess gas.

A wide variety of means are available for monitoring the contents of bioreactor 210. For example, the bioreactor advantageously has a sterilizable sight glass 228 with an adjacent light source 229. Detector 231 can be used for monitoring foam and/or the upper level of the bioreactor contents, while detector 232 is a low-level detector. The bioreactor may have a light source 233 and a top sight detector 234 for visually monitoring the contents from the top. Sample valves 240 may also be provided in the wall of the bioreactor 210. Probe ports 224, 225 and 226 are available for monitoring such parameters as temperature, pH, dissolved oxygen and dissolved carbon dioxide. If desired, multiple probe ports for one or more of these parameters may be employed for added reliability and accuracy.

Tandem bioreactors, each incorporating PFCS, are advantageously used at discrete stages of the culture process. Emulsifying agents may be used to promote dispersion of the PFC in the continuous phase (aqueous) and also allow direct dispersion of PFC bubbles within the vessels without added surfactant and/or excessive agitation. The use and mode of delivery of PFCs is based on the specific requirements of each process step.

Each of the bioreactors operates under perfusion conditions allowing introduction of fresh nutrients and withdrawal of spent, perfused liquid to be reclaimed and reused to the extent necessary. This feature avoids the accumulation of inhibitors and factors toxic to cellular maintenance, expansion and differentiation. PFCs are perfused into each bioreactor on demand. By on demand, it is meant that PFCs are added, under process control, so as to maintain the level needed for gas retention and exchange with the cells, based on dissolved oxygen and/or dissolved carbon dioxide concentration(s) of the media. The PFCs provide a non-shear source of oxygen, a transfer medium for carbon dioxide, and a reservoir for other, e.g. inert gases which may be of use. Fluid containing normal nutrients entering the vessel are removed after a residence time designated for the process step. Designated residence time is the time duration of fluid entering and leaving the bioreactor and is approximately equal to the volume of fluid in the bioreactor divided by the flow rate in volume/unit of time. It is determined by the kinetics in uptake of nutrients, including growth factors, and release of cellular products, which may be inhibitory. Such flow in and flow out may be effectively continuous or semi-continuous in order to exchange media. The rate of culture replenishment is optimized for cellular expansion and/or differentiation. Media replacement range may be as low as about 10% of the total media in a cycle time which may last three months to as much as about 50% replacement in a day. Specific components in the media are selectively used and are to be replaced either continuously or in discrete pulses. A typical process may require 10–100% replacement in a cycle time that may last one to four weeks. The perfusion adds fresh nutrient, but also has the effect of eliminating wastes, e.g. lactate. The perfused fluid is purified and sterilized before reuse and is discarded at specified rates through the use of a drag stream.

The rheological conditions established by the PFC system provide a desirable environment for cellular expansion, differentiation and maturation. The local environment of the cells is a controlled viscous field which minimizes fluidic shear effects and the close approach of bubbles to the cells, which may cause undesirable damaging surface effects. Added agents, including, for example, pluronic acid, may serve to reduce frictional effects where the liquid and cellular surface meet. Maximal viscosity is achieved when the PFC emulsion constitutes about 10–50%, preferably about 30–40%, e.g. about 35% v/v of the medium. Minimal viscosity control, but adequate gas exchange, is obtained when the PFC emulsion constitutes about 10% v/v of the medium.

The process of the invention may advantageously be fully automated. Parameters such as viscosity dissolved oxygen and dissolved carbon dioxide (affected by rate of addition of PFC emulsion and rate of gas addition to PFC and to medium), temperature, pH, rate of addition of growth and differentiation factors, rate of medium replacement and the like may be controlled by a microprocessor. Sensors provide data to the microprocessor, which, in turn, controls valves, pumps and the like to achieve automated process control.

Viscosity control may be achieved by measuring the power required to agitate the vessel and is preferably under the control of a microprocessor. Gas content in the medium may be measured using redundant electrodes which are connected to monitoring device which measure oxygen, carbon dioxide and pH and optionally send such signals to the microprocessor. The control of the environment and additions such as those provided from a perfluorocarbon working tank where oxygen and carbon dioxide content are regulated, are managed under microprocessor control. Supplemental gas may be added through a sparger diffuser to supplement that from the introduction of PFCS. The PFCs are then preferably recycled for reuse after separation from the cells the aqueous phase and purification.

Figure 1:
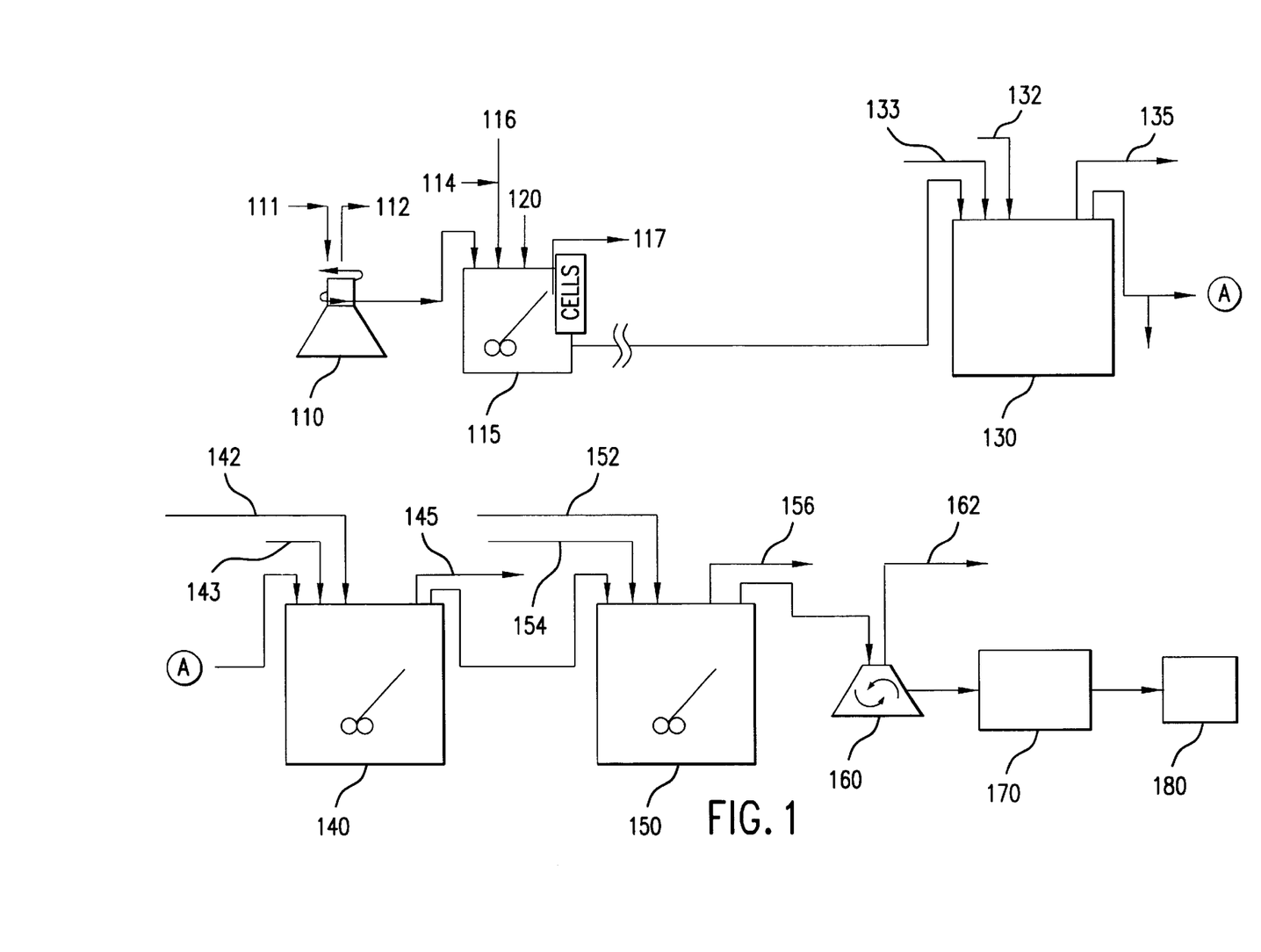
FIG. 1 represents a generalized process diagram. illustrating a preferred embodiment of bioreactor sequences and the use of perfluorocarbons throughout the process.

A flow diagram of a preferred embodiment of the process of the invention is provided in FIG. 1. An inoculum of selected primitive hematopoietic cells is initially cultured in a culture flask 110 (e.g., a conventional shake flask). The cells are cultured in a temperature controlled nutrient medium. The composition of the nutrient medium may be a conventional mammalian cell culturing medium. A preferred nutrient medium, for the cells initially cultured in flask 110, is a serum-deprived medium, modified from that used for culturing murine erythroid progenitor cells, Iscove, et al., *Exp. Cell Res.*, 126:121 (1980), and is described in detail below. Growth factors IL-3 (2–100 ng/mL), IL-6 (1–50 ng/mL) and MGF (5–250 ng/mL) are initially present in the medium used in flask 110 and throughout the expansion in bioreactor 115. During the cell culturing, gas and liquid are perfused into and out of the vessel via lines 111 and 112. Oxygen-saturated perfluorocarbons are added as described above to promote cell expansion without differentiation. After the cells in flask 110 have expanded to about 1000 cells/mL, the cells are separated from the liquid medium and are tansferred to bioreactor 115. As in culture flask 110, the conditions in bioreactor 115 are controlled to cause further expansion of the primitive hematopoietic cells without any significant differentiation. Bioreactor 115 may advantageously be of a design illustrated in FIG. 2. The cells in expansion reactor 115 are maintained in the serum-deprived medium described for culture flask 110, and liquid is perfused into and out of the bioreactor via lines 116 and 117. Growth factors important for cell expansion are IL-3, IL6, and mast-cell growth factor (MGF). These are added in amounts and in timing to maintain concentrations of approximately 20 ng/mL IL-3, 10 ng/mL IL-6 and 50 ng/mL MGF. These concentrations may be increased in order to maximize cell growth or reduced to levels that achieve cell expansion and reduce cost. The concentration of these growth factors fed to the bioreactors are maintained in a range around these levels (IL-3 about 2–40 ng/mL, IL-6 about 1–20 ng/mL and MGF about 5–100 ng/mL) by pulsed, semi-continuous or continuous feeding of nutrients. Feedback data controls the process by monitoring the parameters of cells per unit volume, pH, dissolved oxygen and carbon dioxide, offgas concentrations of ammonia, oxygen, carbon dioxide and lactate and glutamate concentrations. The target cell density for the expansion bioreactor 115 is about 50,000 cells/mL, at which time the number of cells are sufficient to provide the feedstock for further expansion (in volume) in subsequent bioreactors or, if desired, maintained in maintenance bioreactor 130 until ready for further expansion or for differentiation and erythrocyte production. The cells are expanded sufficiently in bioreactor 115 to provide the feedstock needed for erythrocyte production in subsequent steps.

The expanded cells are harvested from bioreactor 115, and, if desired, may be maintained in maintenance bioreactor 130 until ready for differentiation and erythrocyte production. The conditions in maintenance bioreactor 130 may be substantially the same as those in bioreactor 115, except that the rate of addition of growth factors is such as to maintain the cells in culture without substantial expansion or differentiation. Oxygen-saturated perfluorocarbons are added via line 132, and liquid is perfused into and out of maintenance bioreactor 130 via lines 133 and 135. In addition to holding the cells, post-expansion, the maintenance bioreactor serves the function of establishing conditions that allow a large quantity of cells to grow slowly so that they store nutrients and are kept in a healthy state in preparation for the next process phase, which is indicated by the ability of the cells to expand from 1000 to 50,000 cells/mL in 5–7 days. When production of erythrocytes is desired, the expanded primitive hematopoietic cells are harvested from maintenance bioreactor 130 and are transferred to differentiation bioreactor 140.

The conditions in differentiation bioreactor 140 are substantially the same as those in bioreactors 110, 115 and 130, except for the programmed addition of both growth factors and differentiation factors. The major differentiation growth factor is erythropoietin, which is added to the serum-deprived medium used in the previous bioreactors 115 and 130, at a preferred concentration of 3 U/mL. The concentration of erythropoietin is maintained in the range of 0.3 to 6 U/mL, by pulsed, semi-continuous or continuous feeding, until the desired number and population erythroid progenitor cells has been achieved. Dissolved oxygen and carbon dioxide are important in the differentiation step and need to be closely monitored. Other gases, such as nitrogen, may be introduced as part of a stream of sterile air to help maintain a lower level (5–20%) of dissolved oxygen so that differentiation is not inhibited. Oxygen-saturated perfluorocarbons are added via line 142, and liquid media (including growth and differentiation factors) is perfused into and out of the bioreactor via lines 143 and 145. The culturing in bioreactor 140 is continued until the desired population of mature erythroid progenitor cells has been produced.

The mature erythroid progenitor cells are harvested from bioreactor 140 and are transferred to maturation bioreactor 150. Again, the conditions in maturation bioreactor 150 are substantially the same as in the previous bioreactors, except that growth and differentiation factors are not added, but maturation factors are introduced in a programmed manner. Advantageously, the only growth factor that need be used in the maturation bioreactor 150 is erythropoietin, which is added to the serum-deprived medium (without IL-3, IL-6 and MGF) at a preferred concentration of 30 U/mL. The concentration of erythropoietin is maintained in the range of 3 to 60 U/mL by pulsed, semi-continuous or continuous feeding until the desired population of mature erytyrocytes has been obtained. Oxygen-saturated perfluorocarbons are added via line 152 and liquid media is perfused into and out of the bioreactor via lines 154 and 156.

Cells are cultured in maturation bioreactor 150 until the desired population of mature erythrocytes has been obtained. The harvested erythrocytes are then transferred to a cell separator and after washing to remove residual nutrient media, proteins and the like, the cells are transferred to a purification stage 170. For example, cells may be bulk separated in a microfiltration device (Millipore Corp., Bedford, Mass.). In this device, the cells are passed into tubes and media is washed through the walls of the tubes by filtration and the cells are recirculated. Fluid used in washing the cells is adjusted in osmolality (e.g. sterile isotonic saline, supplemented with acid-citrate-dextrose) so that the cells do not rupture. The wash fluid is filtered from the slurry at least three passes in the microfiltration device until culture media is removed. Also, cells may be separated and washed at a bulk level in an automated cell separator (Haemonetics, Inc.) Cells may be further washed and separated, e.g., 3 times, in a centrifugal cell separator (Haemonetics, Inc.). The cells are then resuspended and diluted in sterile acid-citrate-dextrose for storage at a packed cell volume of 70–80% hematocrit, which is approximately 8 billion red cells/mL. In the next steps for use, the cells are uniformly suspended and 250 mL are aseptically transferred to sterile blood-dispensing bags (American Red Cross). The bags are then irradiated with gamma radiation (2000–3000 rads) to destroy coincidental nucleated cells and to insure sterility. At stage 180, the formulated cells are packaged, for example in conventional blood bags. After suitable quality assurance tests, the cells are ready for use in transfusion applications.

Fluid transfer such as between the vessels shown in FIG. 1 will preferably be under use of inert gas pressure and transfer rates which reliably move fluid from one vessel to another at minimal shear. Again. the incorporation of Theological control agents, such PFC emulsions, are used to minimize frictional shear effects at piping walls.

Figure 3:
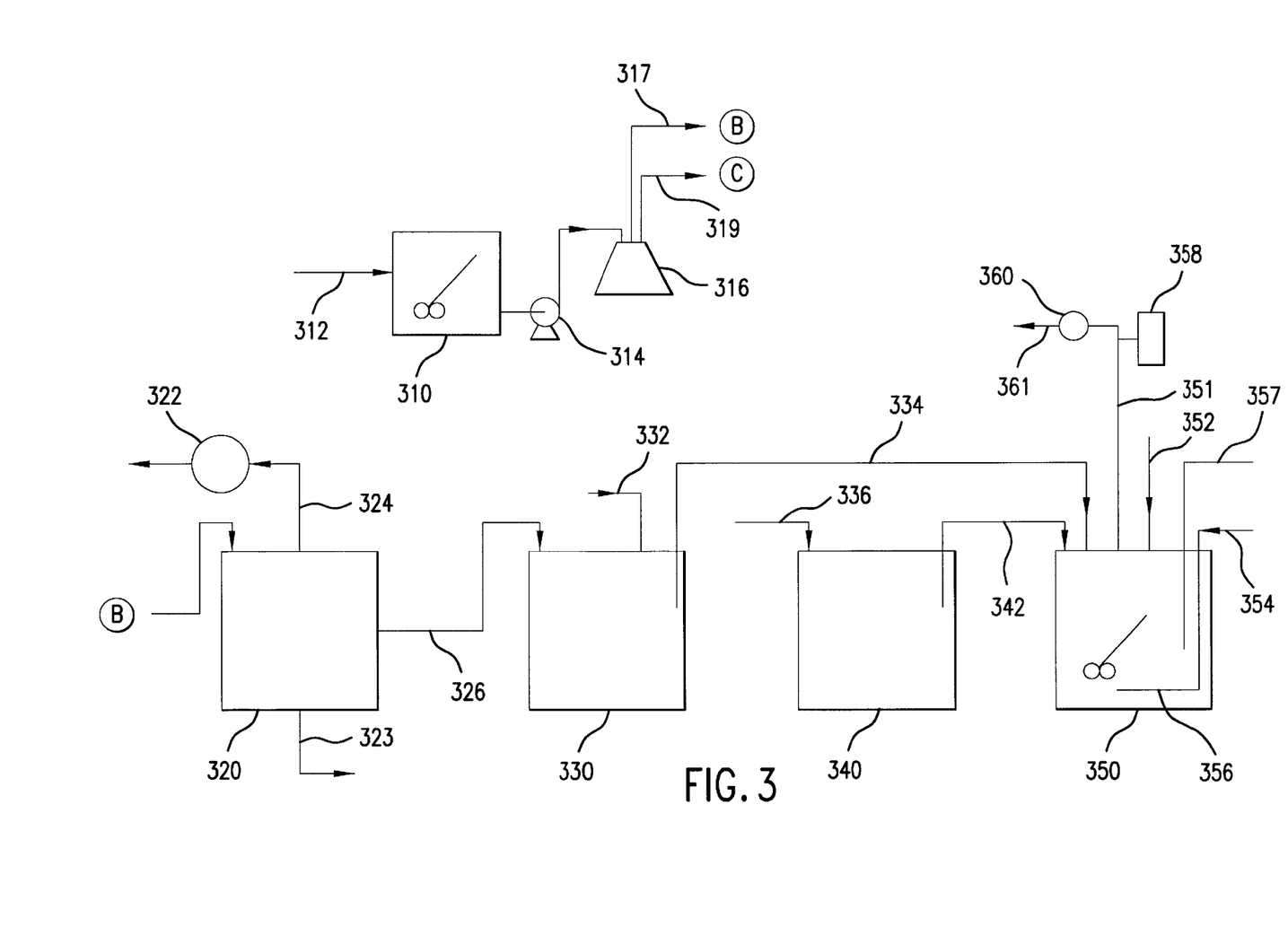
FIG. 3 illustrates a preferred embodiment of a process for the use and reclamation of perfluorocarbons in the process.

FIG. 3 illustrates schematically the treatment of perfusion liquid exiting the bioreactors. It is desirable to recover the PCS for reuse and avoid its release into the atmosphere both for economic and environmental reasons. A preferred embodiment for reclamation of PFCs is shown in FIG. 3. Perfused liquid from a bioreactor is transferred to a hold vessel 310 via line 312. This perfused liquid may then be pumped by pump 314 to a PFC separator 316. The separator is preferably a hydroclone or centrifuge type separator which separates the PFC from the aqueous medium based upon density differences. The aqueous fraction of the perfusion liquid exits the separator 316 via line 319 and may be sent to a perfusion liquid reclamation/treatment process C (see FIG. 4). The spent PFCs exit the separator via line 317 and are sent to a PFC reclamation/treatment process B. As illustrated in FIG. 3, the first step in the PFC reclamation/treatment process involves a liquid-liquid extractor 320. The oily PFC phase is contacted with a water-insoluble organic solvent which extracts the PFC, separating it from the aqueous phase and residual impurities. The PFC is then recovered from the organic solvent, volatile gases are removed via line 324 scrubbed using scrubber 322. The scrubber 322 removes impurities to the extent that waste gas can be exhausted to the atmosphere. The impurities are removed via line 323 and disposed of in an appropriate waste treatment facility. The reclaimed purified PFC is transferred via line 326 to holding tank 330. Vessel 350 is the PFC supply vessel for providing PFCs to each of the bioreactors. As illustrated in FIG. 3, PFC is provided to vessel 350 both in the form of reclaimed PFC from holding tank 330 via line 334 and from a fresh source of PFC held in tank 340 via line 342. In each case, the preferred method of transfer involves pressurizing the tanks with inert gas introduced through lines 332 and 336.

Oxygen is introduced into the PFCs through line 354 and the perforated sparging line 356. Line 352 is used for pressurization of line 350 with an inert gas, and the oxygen-containing PFC is transferred to bioreactors via line 357. The transfer advantageously is controlled by a microprocessor which directs the overall process. Off gases are vented from vessel 350 through line 351. A gas composition detector 358 detects and monitors exhaust for the process and environmental control purposes, to avoid waste loss of PFCs to the atmosphere and the possible release of a pollutant. The off gases pass through trap 360 for the recovery of entrained PFC. The gases, now free of PFCs, may simply be vented.

Figure 4:
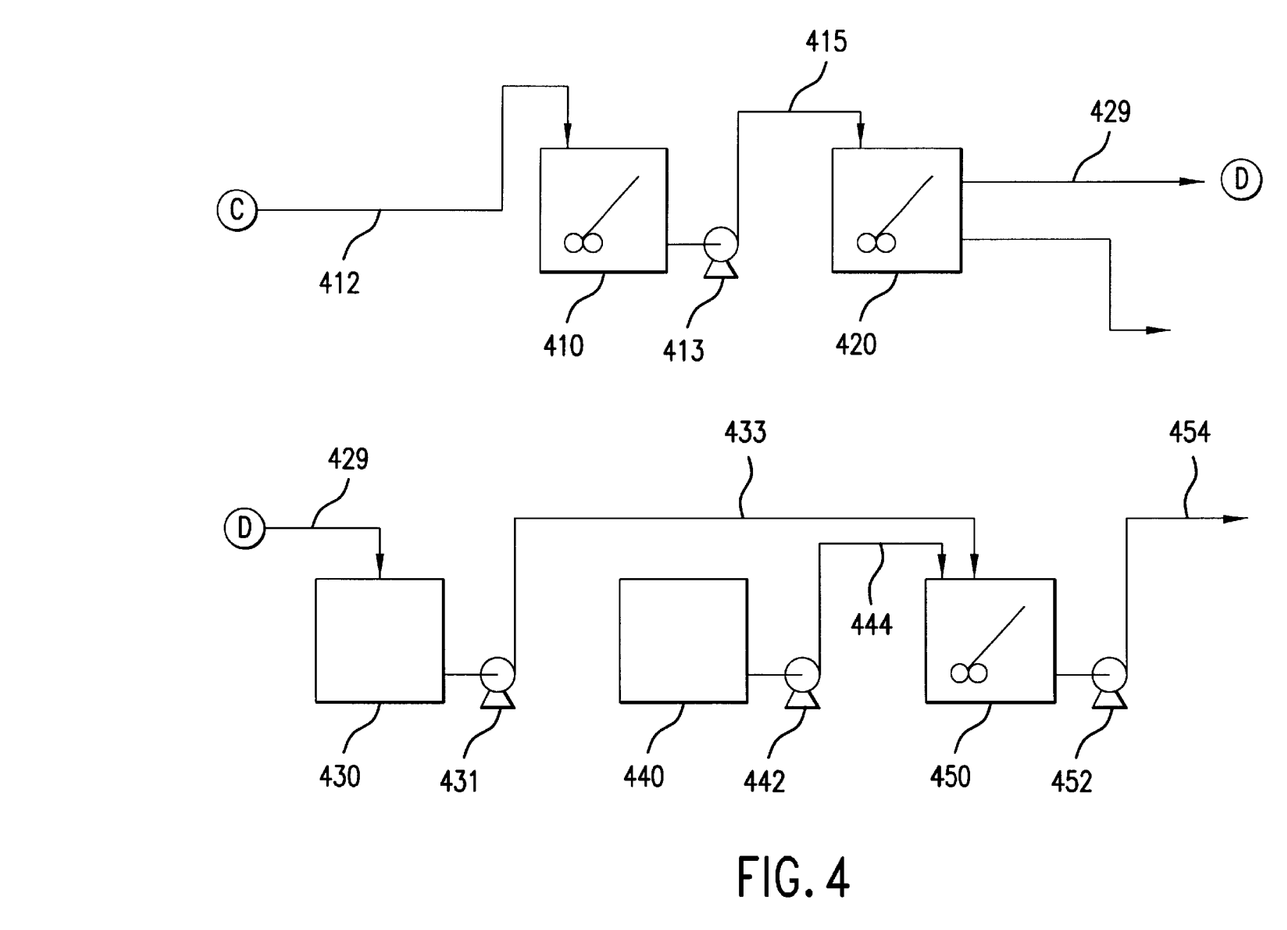
FIG. 4 illustrates a preferred embodiment of the recovery and supply of growth factors and nutrients in this process.

As discussed above, the bioreactors employed in the process of this invention are operated in the perfusion mode, with aqueous medium being replaced throughout the cell-culturing process. Aqueous perfusion liquid removed from the bioreactors contains not only impurities and waste products that are harmful to the cells, but contains valuable growth factors and PFCs. Advantageously, these materials are recovered from the perfusion liquid and recycled to the bioreactors. A preferred embodiment of this recovery process is illustrated in FIG. 4. Aqueous perfusion liquid is transferred via line 412 to return vessel 410, where it is held pending further treatment. The perfusion liquid is pumped from tank 410 using pump 413 and transferred through line 415 to purification means 420. Purification means 420 separates growth factors and differentiation factors from impurities and liquids. Column chromatography, gel filtration, ion exchange, reverse phase and affinity, may be used in succession to recover growth factors. A liquid-liquid extraction, employing polyethylene glycol in one phase, where needed, may be used before chromatography to lessen the load on the columns. The purified growth and differentiation factors are transferred via line 429 to reclaimed factor holding vessel 430. It will be appreciated that separate vessels are used for holding growth factors, differentiation factors and maturation factors. For simplicity, the process is illustrated for one type of factor only. The reclaimed factor is pumped from holding tank 430 using pump 431 transferred via line 433 to the factor working vessel 450. Fresh growth factor, which is held in tank 440, also is used for supplying factors to the factor working vessel 450. The factor is transferred from working vessel 450 to the appropriate bioreactor via pump 452 and line 454. As will be appreciated by those skilled in the art, the factor may be added separately, or in combination with other factors or in combination with other nutrients, as appropriate for the particular process step being performed. Advantageously, the transfer of these factors is under control of a microprocessor.

The invention is further illustrated by the following examples, which are not intended to be limiting.

Expanding Purified Primitive Hematopoietic Cells in a Bioreactor

Serum-deprived medium (i.e. medium which only contains defined, purified proteins of known concentration and quality) used in the expansion bioreactor, is a modification of serum-free medium used for murine erythroid progenitor cells. Iscove, et al., *Exp. Cell. Res.*, 126: 121 (1980). IMDM powder (17633, Sigma Chem. Co., St. Louis, Mo.) is stored at −20° C. in 0.177 g aliquots. Single aliquots are dissolved in 9.8 mL double distilled water plus 0.2 mL 70., (wa/) NaHCO3. A volume of 7.57 mL of this solution is used to prepare 10 mL complete serum-deprived medium by adding 2.3 mL of an albumin/insulin/transferrin/pen/strep mixture (described below), 50 pL of 10 mM 2-mercaptoethanol, and 80 µL of low-density lipoproteins (5 mg/mL, L2139, Sigma Chem. Co., St. Louis. Mo.). Complete serum-deprived medium is sterile filtered (0.2 µm) before use and prepared fresh from powder for each use.

The ingredients of the albumin/insulin/transferrin/pen/ strep mixture are prepared as follows: A solution of 20% (w/v) of BSA (fraction V, A4503, Sigma Chem. Co., St. Louis. Mo.) in double-distilled water is deionized using 60 g of AG-501-X8(D) resin (Bio Rad Laboratories, Richmond, Calif.), filtered and mixed with an equal volume of double-strength IMDM (plus bicarbonate) to give a 10% (w/v) stock solution, which is filter sterilized, and kept at −20° C. in aliquots. Insulin (40205, Collaborative Research, Bedford, Mass.) is stored in aliquots at 1 mg/mL in IMDM at −20° C. Human transferrin (iron-saturated, 82–343, ICN lmmunoBiological, Costa Mesa, Calif.) is stored in aliquots at 20 mg/mL in IMDM at −20° C. A stock solution of penicillin (104 U/mL) and streptomycin (5 mg/mL) is also kept at −20° C. in aliquots (pen/strep). To 20 mL of the 10%, albumin solution, 1 mL of pen/strep stock solution, 1 mL insulin stock solution and 1 mL of transferrin stock solution are added to obtain albumin/insulin/transferrin/pen/strep mixture. Aliquots of 2.3 mL of this mixture are kept at −20° C. to prepare serum-deprived medium described above.

The medium is supplemented with the following recombinant human growth factors prior to use IL-3 20 ng/mL (Amgen)-IL-6, 10 ng/mL (Immunex, Seattle, Wash.) and mast cell growth factor, 50 ng/mL (MGF, Immunex, Seattle, Wash.).

A stirred suspension (expansion) bioreactor is seeded with the serum-deprived medium containing purified hematopoietic cells at a concentration of 1000 cells/mL. The suspension, with continuous stirring, is incubated at 37° C., with 5–20% oxygen and 2–10% carbon dioxide provided by an equilibrated emulsified perfluorocarbon carrier (e.g. Fluosol-DA® Green Cross Ltd.). The culture is monitored for cell density and harvested when the hematopoietic cell concentration reaches 50,000 cells/mL approximately 5–7 days.

Aliquots of expanded cells are (1) frozen by the above procedure for archival purposes, (2) diluted to a concentration of 1000 cells/mL with serum-deprived medium, and placed in second expansion bioreactor at a volume fifty-fold greater than the initial bioreactor and similarly processed until the cells reach a concentration of 50,000 cells/mL. The fifty-fold expansion procedure, with concomitant increase in volume, is repeated twice more, resulting in a final cell concentration of 50,000/mL in a volume 2500 fold-greater than the volume of the initial expansion bioreactor. At this point, the cells are diluted to a concentration of 1000 cells/mL, with maintenance medium (Drouet, et al., *Br. J. Haematol*, 73:143 (1989)), and are transferred to a stirred suspension (maintenance) bioreactor.

The suspension, with continuous stirring, is incubated at 37° C., with 5–20% oxygen and 2–10% a carbon dioxide provided by an equilibrated, emulsified perfluorocarbon carrier. The cultures are monitored for cell growth and are diluted to the original cell concentration if the cell concentration increases to 10,000 cells/mL. At 5–7 day intervals, the cultures are subjected to half medium change with fresh maintenance medium and growth factors.

Prior to seeding the differentiation bioreactor, an aliquot of cells are transferred to the expansion bioreactor for an additional fifty-fold expansion of the cell concentration, using the procedure described above.

Seeding Bioreactor for Differentiation

Prior to seeding the differentiation bioreactor, the serum-deprived medium containing the expanded cells (from the expansion bioreactor), is supplemented with erythropoietin at a final concentration of 3 u/mL. The differentiation bioreactor is a continuously stirred vessel, incubated at 37° C., with 5–20% oxygen and 2–10% carbon dioxide provided by an equilibrated, emulsified perfluorocarbon carrier. The culture is monitored for cell growth and cell type. After approximately 10–20 days, the cell concentration is expanded 10,000-fold and the cells are 99% CD34–, CD71+, indicating that the cells have not only increased greatly in number, but also have differentiated into a relatively late erythroid stage.

Seeding Bioreactor for Maturation

Cells from the differentiation bioreactor are transferred to the maturation bioreactor where the serum-deprived medium is supplemented with only erythropoietin at a final concentration of at least 30 $\mu$/mL. The differentiation bioreactor is a continuously stirred vessel, incubated at 37° C., with 5–20% oxygen and 2–10% carbon dioxide provided by an equilibrated, emulsified perfluorocarbon carrier. The culture monitored for cell type. When the cells are predominately (e.g.>90%) enucleated, polychromic or orthochromic normoblasts, the entire culture is harvested.

Harvesting and Separation of Mature Cells

The harvest from the maturation bioreactor is allowed to settle for 1–3 hours at 4° C. to allow the red cells to settle and separate from the medium. After complete settlement, the medium is withdrawn and the cells are aseptically washed at least three times with sterile saline (NaCl, 9 g/L), using an automated blood cell processor (Haemonetics, Inc.), incorporating a protocol programmed for leukocyte and thrombocyte depletion. After the third wash-step, the cells are resuspended and diluted in sterile acid-citrated dextrose (ACD) diluent for storage at a packed cell volume (hematocrit) of 70–80% or, assuming normal morphology, 8 billion cells/mL. Prior to use the cells are uniformly suspended and 250 mL are aseptically transferred to sterile blood-dispensing bags (e.g. American Red Cross). The bags are then irradiated with a gamma radiation source (2000–3000 rads) to destroy coincidental nucleated cells and to ensure sterility.

Characterizing and Using the Composition

The final product is characterized for suitability as a clinically effective transfusable composition. Using standard blood-banking procedures, the cells are tested (typed) for the specified red blood cell antigens and are found to be absent, the same as determined for the blood of the hematopoietic cell donor, thus confirming the universal properties of this composition.

In addition to blood type and immunocompatibility, other physical characteristics also affect the suitability of these cells as a clinically effective transfusable composition. These characteristics include the size, volume, number and degree of maturity of the cells that make up the composition of this invention. The size, volume and number are determined in a clinical laboratory employing standard blood cell counting procedures, for example, using Coulter Counter technology (Coulter Diagnostics, Hialeah, Fla.). Reticulocytes are also determined by Coulter Counter technology and are found to be within clinical norms. These parameters indicate that the cells of this invention are within the size and volume range consistent for use as a transfusable composition. Microscopic examination of a dried smear of the cells, stained with Wright's stain, also confirms that mature red blood cells are the predominate cell type and that nucleated cell types are absent, confirming the degree of maturation and suitability as a clinically effective transfusable composition.

A primary indicator of the cells' ability to perform physiologically as a transfusable, oxygenating composition is based on the carbonic anhydrase activity of the cells. The cells of this invention are tested for carbonic anhydrase using radioassay and are found to be within normal adult limits for both the B and C isoenzymes. Wahlstrand, et al., *Scand. J. Clin. Lab. Invest.*, 39: 503 (1979). These levels of carbonic anhydrase activity indicate that the cells of this invention are adequate for performing the oxygen and carbon dioxide exchange needed as a clinically effective transfusable composition. The invention, now fully disclosed, it will be apparent to one of ordinary skill in the art that many changes and modifications can be made thereto without departing from the spirit or scope of the appended claims.

What is claimed is:

1. A process for producing a transfusable, oxygenating composition of red blood cells which comprises:

(a) expanding a culture of purified primitive hematopoietic cells in a first bioreactor in the presence of a growth factor and under conditions which promote self renewal of such cells to increase their numbers without substantial differentiation into committed progenitor cells, thereby producing an expanded culture of purified primitive hematopoietic cells;

(b) effecting differentiation of the primitive hematopoietic cells by culturing said expanded culture of purified primitive hematopoietic cells in a second bioreactor in the presence of a differentiation factor and under conditions that promote the differentiation of the primitive hemopoietic cells into erythroid cells;

(c) producing mature erythrocytes by culturing erythroid progenitor cells in a third bioreactor in the presence of a maturation factor and under conditions that promote the maturation of the progenitor erythroid cells into the mature erythrocytes; and (d) harvesting said mature erythrocytes and formulating them into a transfusable oxygenating composition.

2. The process of claim 1 wherein said mature erythrocytes exhibit carbonic anhydrase activity.

3. The process of claim 1, wherein the primitive hemopoietic cells employed in step (a) are obtained from a donor having a blood type compatible with that of an intended recipient of the cells.

4. The process of claim 3, wherein the blood type of the donor is type O, Rh negative.

5. The process of claim 3, wherein the blood type of the donor is Rh negative, type A, type B, type AB or type O.

6. The process of claim 3, wherein the primitive hemopoietic cells employed in step (a) are obtained from a donor that is negative for the following red blood cell antigens: A, B, D (Rh), Le$^a$, Le$^b$, K, E, P$_1$, c, cE, Fy$^a$, M, jK$^a$, S, Ce, E, jK$^b$, N, s, Fy$^b$.

7. The process of claim 1, wherein the purified hemopoietic cells produced in step (a) exhibit the phenotype CD34+, CD45RAlo, CD71lo.

8. The process of claim 1, wherein the media used in each of the bioreactors is serum-deprived.

9. The process of claim 1, wherein the first bioreactor contains a nutrient medium supplemented with one or more of the following recombinant human growth factors: IL-3, IL-6 and mast cell growth factor.

10. The process of claim 1, wherein the second bioreactor contains a nutrient medium supplemented with recombinant human IL-3, IL-6, mast cell growth factor and erythropoietin.

11. The process of claim 1, wherein the third bioreactor contains erythropoietin and is substantially devoid of other growth and differentiation factors.

12. The process of claim 1, wherein the nutrient media in each of the bioreactors contains sufficient perfluorocarbons to improve the exchange of oxygen and carbon dioxide between the cells and the nutrient media.

13. The process of claim 12, wherein the perfluorocarbons are introduced in the form of an emulsion which serves the additional function of increasing the viscosity of the medium.

14. The process of claim 12, wherein the perfluorocarbons contain from about 5 to about 20% oxygen and from about 5 to about 10% carbon dioxide.

15. A method for producing a transfusable, oxygenating composition of red blood cells, which comprises:
   (a) obtaining from a human donor primitive hematopoietic cells, wherein said human donor is a blood type O, Rh factor negative universal donor;
   (b) incubating said primitive hematopoietic cells in a bioreactor in a nutrient medium containing recombinant human growth factors, recombinant human differentiation factors or recombinant human maturation factors to produce an expanded culture of universally compatible human erythrocytes; wherein said nutrient medium contains sufficient perfluorocarbons to improve the exchange of oxygen and carbon dioxide between said cells, and said medium; and
   (c) harvesting said erythrocytes.

16. The process of claim 15, wherein said donor is negative for the following red blood antigens: A, B, D (Rh), $Le^a$, $Le^b$, K, E, $P_1$, c, cE, $Fy^a$, M, $jK^a$, S, Ce, E, $jK^b$, N, s, $Fy^b$.

17. The process of claim 15, wherein the perfluorocarbons contain from about 5 to about 20% oxygen and from 2 to about 10% carbon dioxide.

18. The process of claim 15, wherein the perfluorocarbons are introduced into the nutrient medium in the form of an emulsion which serves for the purpose of improving the viscosity of the medium.

19. The process of claim 15, wherein said growth factors are selected from the group consisting of human recombinant IL-3, IL-6 and mast cell growth factor.

20. The process of claim 15, wherein the differentiation factors in clude human recombinant IL-3, IL-6, mast cell growth factor and erythropoietin.

21. The process of claim 15, wherein the maturation factor includes human recombinant erythropoietin.

22. The process of claim 15, wherein said hematopoietic cells exhibit the phenotype CD34+, CD45, RAlo, CD71lo.

* * * * *